United States Patent
Harrah et al.

(10) Patent No.: US 10,376,284 B2
(45) Date of Patent: Aug. 13, 2019

(54) DEVICES FOR CONTROLLED SOFT TISSUE HYDRODISSECTION

(71) Applicant: Boston Scientific Scimed, Inc., Maple Grove, MN (US)

(72) Inventors: Timothy P. Harrah, Cambridge, MA (US); Jozef Slanda, Milford, MA (US); Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 212 days.

(21) Appl. No.: 14/674,933

(22) Filed: Mar. 31, 2015

(65) Prior Publication Data

US 2015/0283325 A1    Oct. 8, 2015

Related U.S. Application Data

(60) Provisional application No. 61/974,778, filed on Apr. 3, 2014.

(51) Int. Cl.
| | |
|---|---|
| *A61B 17/42* | (2006.01) |
| *A61B 17/3203* | (2006.01) |
| *A61M 5/315* | (2006.01) |
| *A61B 90/00* | (2016.01) |

(52) U.S. Cl.
CPC .......... *A61B 17/42* (2013.01); *A61B 17/3203* (2013.01); *A61M 5/31505* (2013.01); *A61B 2090/034* (2016.02); *A61B 2090/08021* (2016.02); *A61M 2210/1475* (2013.01)

(58) Field of Classification Search
CPC ............ A61B 17/42; A61B 2090/034; A61M 5/31505; A61M 2210/1475
See application file for complete search history.

(56) References Cited

U.S. PATENT DOCUMENTS

| | | | | |
|---|---|---|---|---|
| 2,198,666 A | * | 4/1940 | Gruskin | A61M 5/31551 222/309 |
| 3,835,835 A | * | 9/1974 | Thompson | A61B 5/15003 600/575 |
| 5,115,816 A | * | 5/1992 | Lee | A61M 5/1782 600/562 |
| 6,368,305 B1 | * | 4/2002 | Dutton | A61M 5/31501 604/192 |
| 2012/0022447 A1 | * | 1/2012 | Oliver | A61M 5/3234 604/110 |
| 2012/0033027 A1 | | 2/2012 | Murphy | |

FOREIGN PATENT DOCUMENTS

EP           446403 A1    9/1991

* cited by examiner

*Primary Examiner* — Bradley J Osinski
(74) *Attorney, Agent, or Firm* — Brake Hughes Bellermann LLP

(57) ABSTRACT

A medical device including a brake having a housing member and an actuation member. The housing member has a receiving portion and is configured to be removably coupled to a syringe. The actuation member is movably coupled to the housing member.

18 Claims, 8 Drawing Sheets

US 10,376,284 B2

DEVICES FOR CONTROLLED SOFT TISSUE HYDRODISSECTION

CROSS-REFERENCE TO RELATED APPLICATION

This application is a Nonprovisional of, and claims priority to, U.S. Patent Application No. 61/974,778, filed on Apr. 3, 2014, entitled "DEVICES FOR CONTROLLED SOFT TISSUE HYDRODISSECTION", which is incorporated by reference herein in its entirety.

TECHNICAL FIELD

This disclosure relates generally to medical devices and surgical procedures, and particularly medical devices and methods used to dissect bodily tissue such as in a procedure to prepare a patient's body to receive a bodily implant.

BACKGROUND

Bodily implants, such as mesh implants, are sometimes placed within a body of a patient. For example, sometimes implants are placed within a body of a patient to provide support to portions of the body of the patient. Implants may be placed in a pelvic region of a patient to provide support to portions of the pelvic region of the patent.

In some procedures for placing implants within a body of a patient, an operator dissects a tissue layer and creates a pocket or space for placing the implant or the mesh. For example, a space or pocket may be formed between the vagina and the bladder of the patient. In some cases, the pocket or space may be required because there may not be space for the implant or the mesh in normal tissue. In some cases the dissection procedure is a hydrodissection procedure (or performed using a fluid). In other cases, a different type of dissection procedure is used.

In light of the above, there is a need for a medical device and a method that allows for an effective and efficient dissection procedure. For example, there is a need for a device that allows for a controlled dissection procedure.

SUMMARY

In one embodiment, a medical device including a break having a housing member and an actuation member. The housing member has a receiving portion and is configured to be removably coupled to a syringe. The actuation member is movably coupled to the housing member.

In another embodiment, a medical device includes a syringe and a break. The syringe has a body portion and a plunger that is movably coupled to the body portion. The break has a housing member and an actuation member. The housing member is coupled to the syringe. The actuation member is movably coupled to the housing member.

In another embodiment, a method includes inserting a medical device into a body of the patient, the medical device including a syringe having a body portion and a plunger movably coupled to the body portion, and a break having a housing member and an actuation member; and moving the actuation member with respect to the housing to allow the plunger syringe to move with respect to the body portion of the syringe.

DETAILED DESCRIPTION

Figure 1:
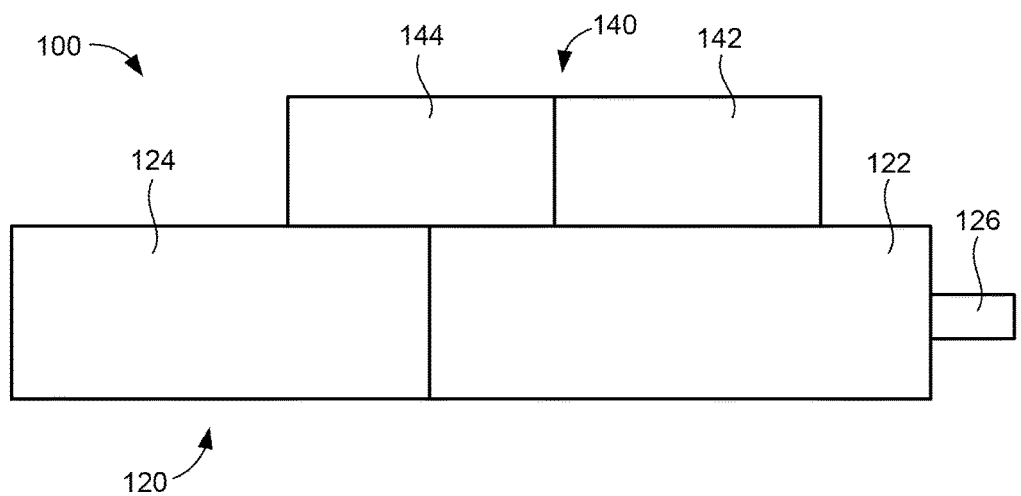
FIG. 1 is a schematic diagram of a medical device according to an embodiment of the invention.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to systems, methods, and devices for locating and dissecting (such as hydrodissecting) any space for various types of procedures such as treating female pelvic prolapse, or anal prolapse in males or females, for example. Also, the systems, methods, and devices described herein may be used for transabdominal and transvaginal dissection, and graft placement (e.g., mesh or biologic graft), as well as dissecting the suburethral plane for sling placement. More generally, the systems, methods, and devices of the embodiments may be used for any procedure for creating a space such as the Vesico-Vaginal-Septum, the Recto-Vaginal-Septum, or the pleural space, among others. In another example, the systems, methods, and devices of the embodiments may be used in the dissection of the prostate during Holmium Laser Ablation of the Prostate. Further, the syringes or injection devices and methods may involve injecting intrathecal antibiotics, steroids, sclerosing agents, and/or any type of fluid, for example.

The term patient may hereafter be used for a person who benefits from the medical device or the methods disclosed in the present application. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

FIG. 1 is a schematic diagram of a medical device 100 configured to perform a dissection procedure. For example, the medical device 100 may be used to prepare a patient's body for receiving a bodily implant (not shown), and/or open a space within the body of the patient for an additional medical procedure.

The medical device 100 of FIG. 1 (or any of the other figures) may be used in any area within the body of the patient such as the pelvic region, the mouth, throat, and/or esophagus. The bodily implant can be a mesh-based device (e.g., a sling), used in the treatment of fecal incontinence, urinary incontinence, prolapse, and other such disorders. In one example, the medical device 100 may be used for opening up spaces between tissues layers before receiving the bodily implant.

In the illustrated embodiment, the medical device 100 includes a syringe 120 and a brake 140. The syringe 120 includes a body or body portion 122 and a plunger 124. The plunger 124 is movably coupled to the body 122. In some embodiments, the plunger 124 is slidably coupled to the body 122. In some embodiments, the plunger 124 may be moved in a first direction with respect to the body 122 to suck or draw fluid into a receptacle, cavity, or chamber defined by the body 122. The plunger 124 may then be moved in a second direction with respect to the body 122 to force the fluid out of the receptacle, cavity, or chamber defined by the body 122.

In some embodiments, the plunger 124 is biased to one of its positions with respect to the body 122. For example, the plunger 124 may be biased to an injection position with respect to the body 122. In such an embodiment, once the fluid is drawn into the receptacle, cavity, or chamber of the body 122, the biasing of the plunger 124 causes the plunger 124 to move with respect to the body 122 to eject the fluid from the receptacle, cavity, or chamber. In some embodiments, the syringe includes a biasing member, such as a spring, disposed between the plunger 124 and the body 122 to provide the biasing.

In some embodiments, the syringe 120 includes a needle member 126 extending from the body 122. The needle member 126 may have any length and may have a tip or distal end portion that is configured to pierce bodily tissue. In some embodiments, the needle member 126 defines a lumen that is in fluid communication with the receptacle, cavity, or chamber defined by the body 122.

The brake 140 includes a housing 142 and an actuation member 144. The actuation member 144 is movably coupled to the housing 142. In some embodiments, the actuation member 144 is pivotally coupled to the housing 142. In other embodiments, the actuation member 144 is slidably or otherwise movably coupled to the housing 142.

In some embodiments, the brake 140 is removably coupled to the syringe 120. For example, in some embodiments, the housing 142 of the brake 140 is removably coupled to the body 122 of the syringe 120. In other words, a user, such as a physician, may couple the brake 140 to the syringe 120 or may decouple the brake 140 from the syringe 120 when it is not desirable to use the syringe 120 with the brake 140. For example, the housing 142 may include a coupling portion that is configured to frictionally mate with or receive a portion of the body 122 to removably couple the brake 140 to the syringe 120. In other embodiments, another coupling mechanism may be used to removably couple the brake 140 to the syringe 120.

In some embodiments, the brake 140 is fixedly coupled to the syringe 120. For example, the brake 140 may be fixedly coupled to the syringe 120 via glue or another adhesive or may be formed integrally with the syringe 120.

The actuation member 144 of the brake 140 includes a contact portion that is configured to selectively contact the plunger 124 of the syringe 120. Accordingly, the movement of the plunger 124 with respect to the body 122 may be controlled by the actuation member 144. In some embodiments, the actuation member 144 is configured to prevent or help prevent movement of the plunger 124 with respect to the body 122 when the contact portion of the actuation member 144 is contacting the plunger 124. In some embodiments, the actuation member 144 is configured to slightly contact the plunger 124 and to slow the movement of the plunger 124 with respect to the body 122.

In some embodiments, the actuation member 144 may be moved to different positions with respect to the plunger 124 to prevent movement of the plunger 124 with respect to the body 122, to slow movement of the plunger with respect to the body 122, or to not interfere with the movement of the plunger 124 with respect to the body 122. For example, in some embodiments, the actuation member 144 may be placed in a first position with respect to the housing 142 to avoid contact with the plunger 124. In this position, the actuation member 144 does not interfere or limit the movement of the plunger 124 with respect to the body 122. The actuation member 144 may be placed in a second position with respect to the housing 142 to slightly contact the plunger 124. In this position, the actuation member 144 is configured to provide some resistance to the movement of the plunger 124 with respect to the body 122. The actuation member 144 may be placed in a third position with respect to the housing 142. In this position, the actuation member 144 contacts the plunger 124 to prevent or help prevent movement of the plunger 124 with respect to the body 122. In some embodiments, the contacting of the actuation member 144 with the plunger 124 provides a frictional force that prevents or helps prevent the movement of the plunger 124 with respect to the body 122.

The brake 140 may be formed of any know material. For example, in some embodiments, the brake 140 is formed of a biocompatible material. In some embodiments, the brake 140 is formed of a plastic or polymer material. The brake 140 and its components may be of any size or shape. For example, a brake that 140 that is configured to be coupled to one type of syringe might be larger or smaller than a brake 120 that is configured to be coupled to a different type of syringe.

In use, the device 100 may be used to perform a dissection procedure, such as a hydrodissection procedure, within a body of a patient. The syringe 120 of the device 100 may be used to collect or suck up a fluid such as water or a saline solution. This may be done by inserting a distal end portion of the needle member 126 of the syringe into the fluid and retracting or moving the plunger 124 proximally with respect to the body 122. Once the fluid is loaded into the syringe 120, a portion of the syringe 120, such as the distal end portion of the needle member 126 of the syringe 120 may be inserted into the body of the patient. Specifically, the needle member 126 of the syringe 120 may be inserted into the body of the patient while the brake 140 is preventing or helping to prevent movement of the plunger 124 with respect to the body 122.

Once the device 100 is appropriately placed within the body of the patient (such as at the desired dissection location), the physician may move the actuation member 144 to disengage or move away from the plunger 124. With the actuation member 144 in this position the plunger 124 may move with respect to the body 122 and force or eject the fluid from the syringe 120. In some embodiments, the ejection of the fluid from the syringe 120 into the body of the patient dissects the tissue disposed proximate the distal end of the needle member 126 of the syringe 120. In some embodiments, the movement of the actuation member 144 with respect to the plunger 124 allows for a controlled dissection of bodily tissue. For example, the actuation member 144 may be moved completely away from the plunger 124 to allow the plunger 124 to move fast with respect to the body 122 and quickly eject the fluid or the actuation member 144 may be moved to a position of slight contact with the plunger 124 to allow the plunger 124 to move more slowly with respect to the body 122 and more slowly eject the fluid from the syringe 120.

FIGS. 2-11 illustrate a medical device 200 in accordance with an embodiment of the invention. In some embodiments, the medical device 200 is configured to perform a dissection procedure. For example, the medical device 200 may be used to prepare a patient's body for receiving a bodily implant and/or open a space within the body of the patient for an additional medical procedure.

The medical device 200 may be used in any area within the body of the patient such as the pelvic region, the mouth, throat, and/or esophagus. The bodily implant can be a mesh-based device (e.g., a sling), used in the treatment of fecal incontinence, urinary incontinence, prolapse, and other such disorders. In one example, the medical device 100 may be used for opening up spaces between tissues layers before receiving the bodily implant.

Figure 2:
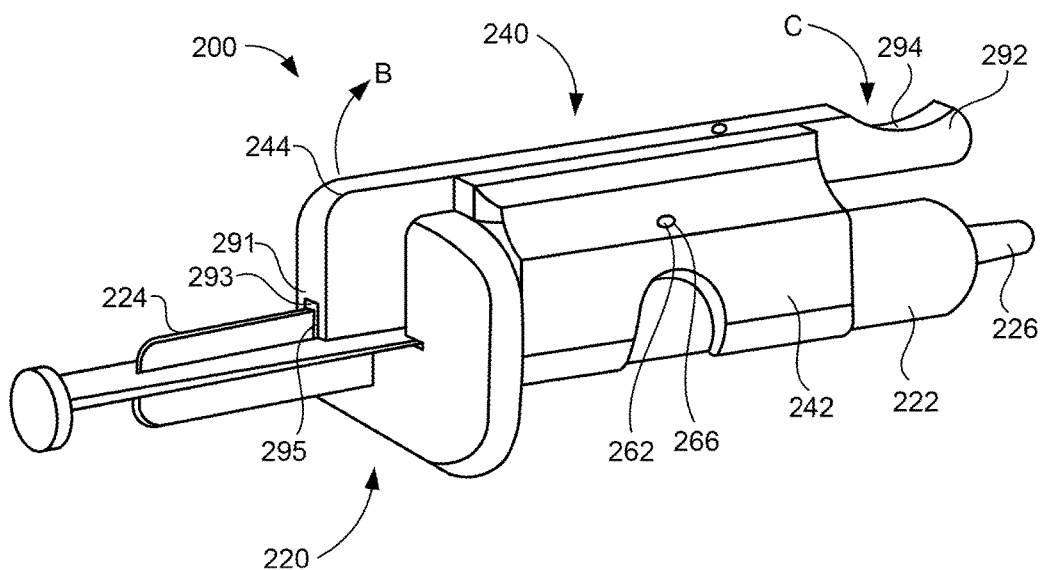
FIG. 2 is a perspective view of a medical device according to an embodiment of the invention.
Figure 3:
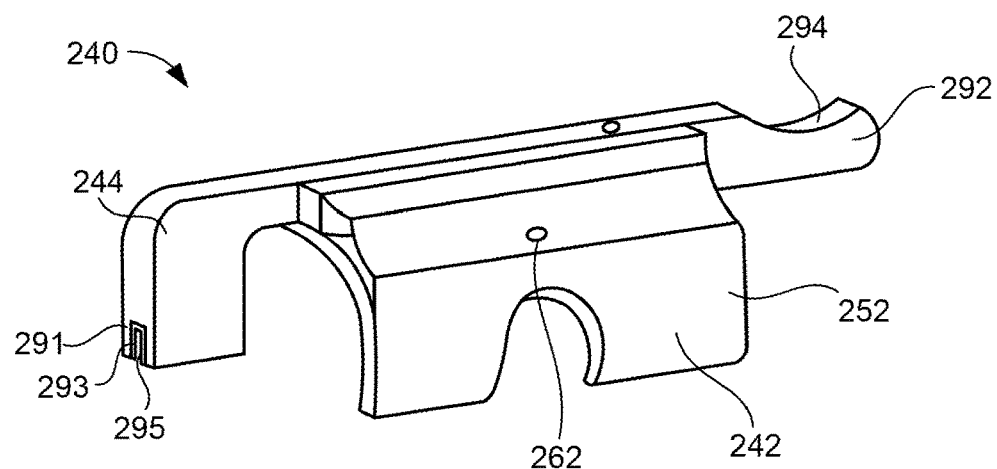
FIG. 3 is a perspective view of a break according to an embodiment of the invention.
Figure 4:
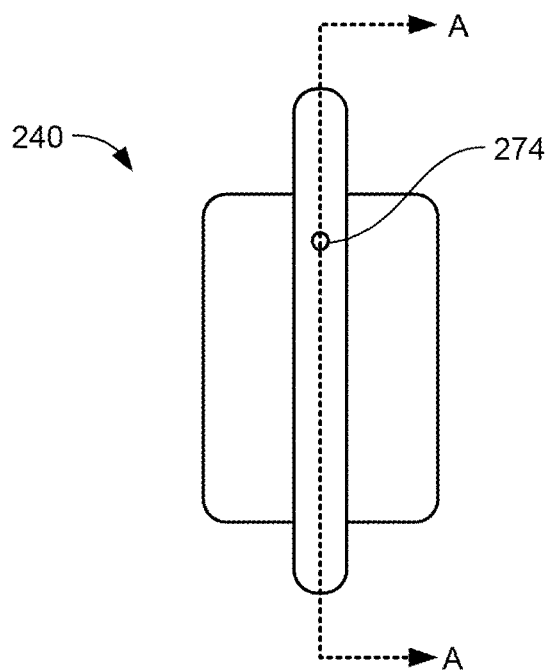
FIG. 4 is a top view of the break of FIG. 3.
Figure 5:
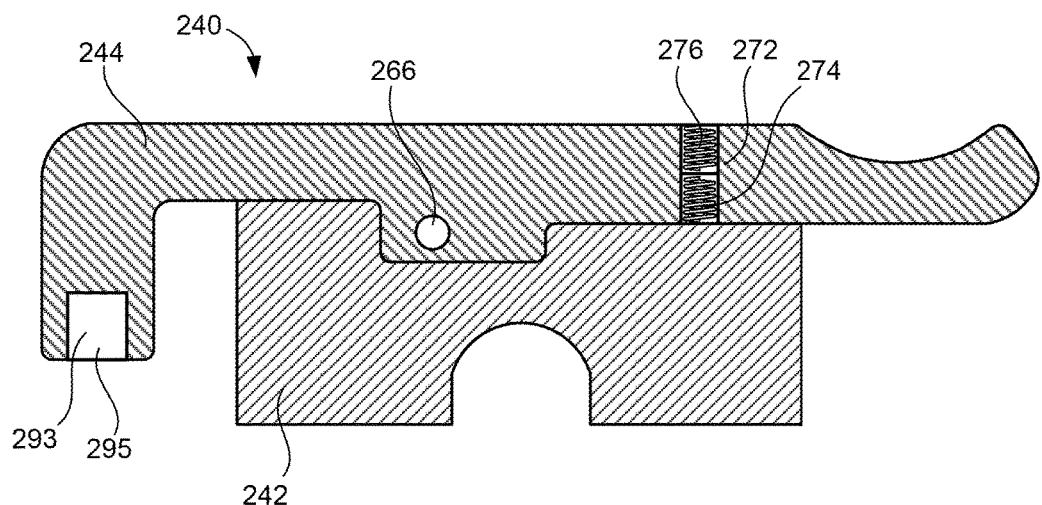
FIG. 5 is a cross-sectional view of the break of FIG. 3 taken along line A-A of FIG. 4.
Figure 6:
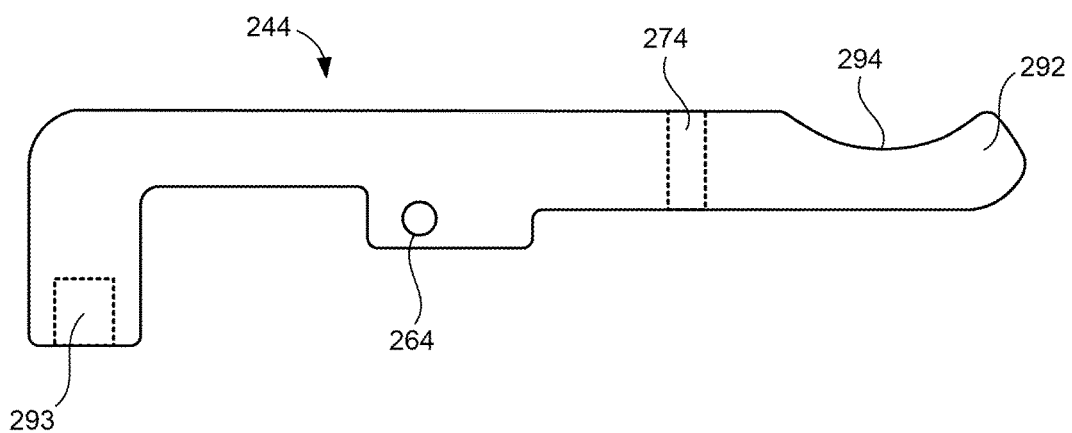
FIG. 6 is a side view of an actuation member of the break of FIG. 3.
Figure 7:
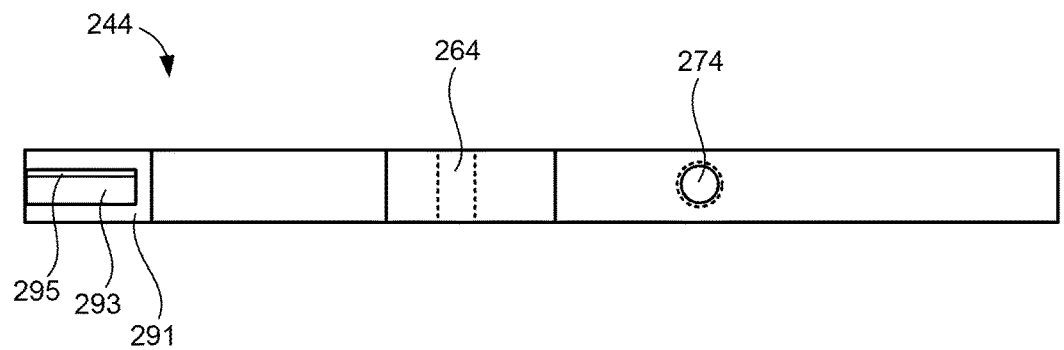
FIG. 7 is a bottom view of the actuation member of FIG. 6.
Figure 11:
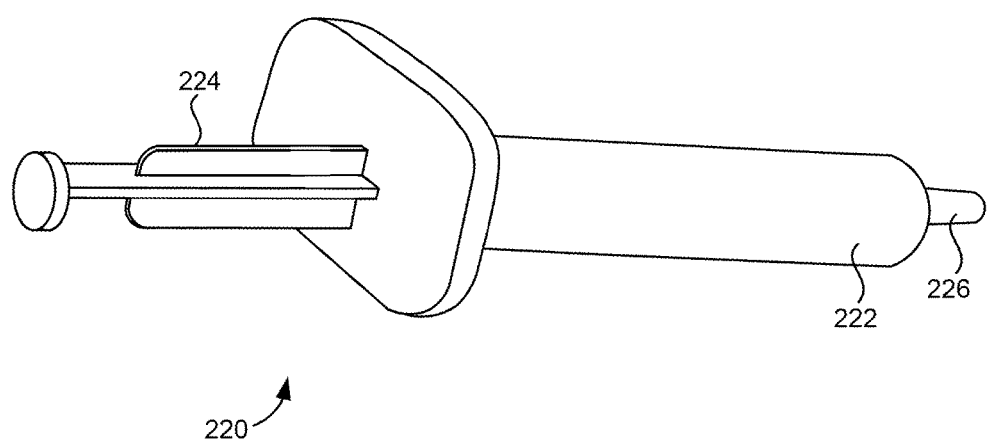
FIG. 11 is a perspective view of the syringe of the medical device of FIG. 2.

In the illustrated embodiment, the medical device 200 includes a syringe 220 and a brake 240. As best illustrated in FIGS. 2 and 11, the syringe 220 includes a body or body portion 222 and a plunger 224. The plunger 224 is movably coupled to the body 222. In some embodiments, the plunger 224 is slidably coupled to the body 222. In some embodiments, the plunger 224 may be moved in a first direction (for example, a proximal direction) with respect to the body 222 to suck or draw fluid into a receptacle, cavity, or chamber defined by the body 222. The plunger 224 may then be moved in a second direction with respect to the body 222 to force or eject the fluid out of the receptacle, cavity, or chamber defined by the body 222.

In some embodiments, the plunger 224 is biased to one of its positions with respect to the body 222. For example, the plunger 224 may be biased to an injection position with respect to the body 222. In such an embodiment, once the fluid is drawn into the receptacle, cavity, or chamber of the body 222, the biasing of the plunger 224 causes the plunger 224 to move with respect to the body 222 to eject the fluid from the receptacle, cavity, or chamber. In some embodiments, the syringe 220 includes a biasing member, such as a spring, disposed between the plunger 224 and the body 222 to provide the biasing.

In the illustrated embodiment, the syringe 220 includes a needle member 226 extending from the body 222. The needle member 226 may have any length and may have a tip or distal end portion that is configured to pierce bodily tissue. The needle member 226 defines a lumen that is in fluid communication with the receptacle, cavity, or chamber defined by the body 222. Accordingly, fluid may enter or exit the receptacle, cavity, or chamber via the lumen defined by the needle member 226.

In some embodiments, the syringe 220 is an epidural syringe. In some embodiments, the syringe 220 is a loss of resistance syringe. For example, in some embodiments, the syringe 220 may be an Episure syringe.

As best illustrated in FIGS. 2-10, the brake 240 includes a housing 242 and an actuation member 244. The actuation member 244 is movably coupled to the housing 242. Specifically, the actuation member 244 is pivotally coupled to the housing 242.

In the illustrated embodiment, the brake 240 is removably coupled to the syringe 220. Specifically, the housing 242 of the brake 240 is removably coupled to the body 222 of the syringe 220. In other words, a user, such as a physician, may couple the brake 240 to the syringe 220 or may decouple the brake 240 from the syringe 220 when it is not desirable to use the syringe 220 with the brake 240.

Figure 8:
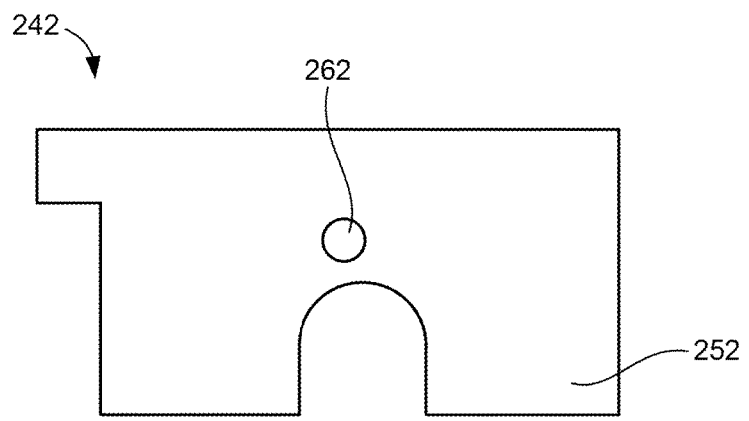
FIG. 8 is a side view of a housing of the break of FIG. 3.
Figure 9:
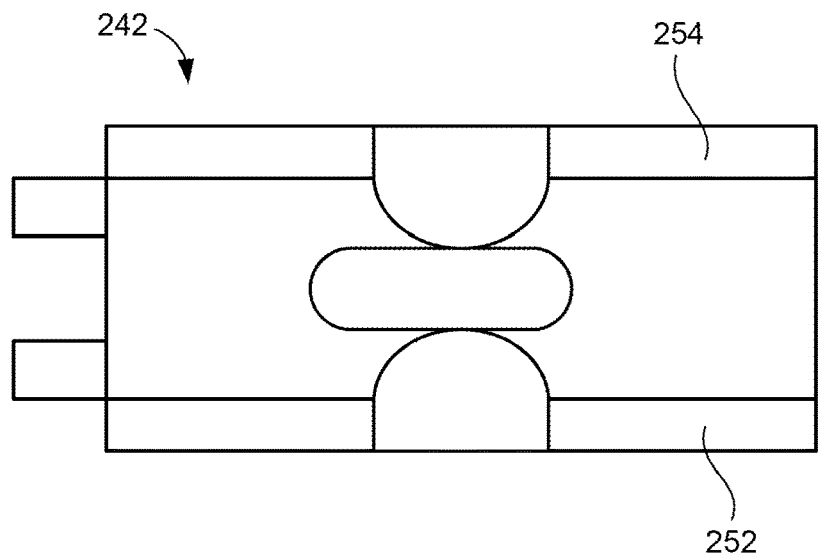
FIG. 9 is a top view of the housing of FIG. 8.
Figure 10:
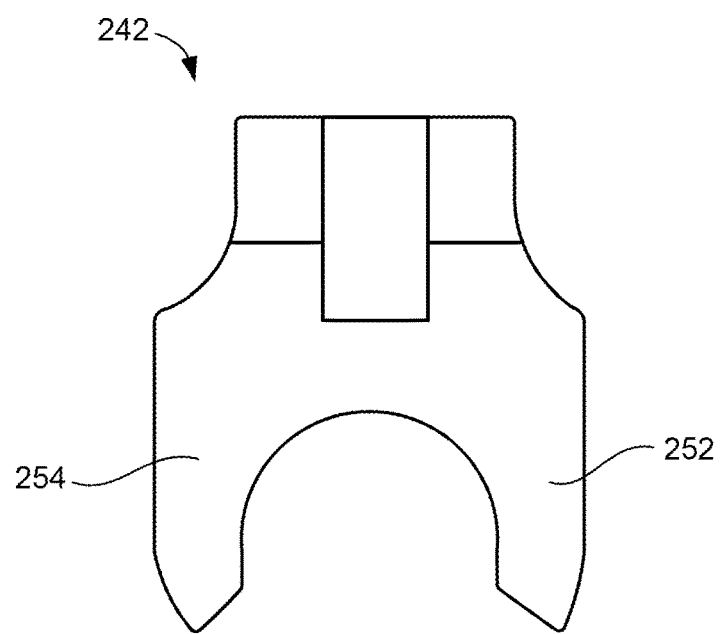
FIG. 10 is an end view of the housing of FIG. 8.

As best illustrated in FIGS. 8-10, in the illustrated embodiment, the housing 242 includes a coupling portion 243 that is configured to frictionally mate with or receive a portion of the body 222 to removably couple the brake 240 to the syringe 220. Specifically, in the illustrated embodiment, the housing 242 includes arms 252 and 254. The arms 252 and 254 extend from a body portion 248 of the housing and define the coupling portion 243. The arms 252 and 254 are configured to extend around and frictionally couple the brake 240 to the syringe 220. In some embodiments, the arms 252 and 254 are configured to flex or bend slightly to facilitate the coupling and decoupling of the brake 240 with the syringe 220.

In the illustrated embodiment, the arms 252 and 254 have curved surfaces such that they define a receiving portion 243 that is round or tubular that is configured to receive a tubular portion of a syringe. In other embodiments, the receiving portion 243 is of a different shape and is configured to receive a different shaped portion of the syringe.

In other embodiments, another coupling mechanism may be used to removably couple the brake 240 to the syringe 220. For example, in some embodiments, the syringe 220 may include a first portion of a clip and the brake may include a second portion of a clip that is configured to be removably coupled to the first portion of the clip.

In some embodiments, the brake 240 is fixedly coupled to the syringe 220. For example, the brake 240 may be fixedly coupled to the syringe 220 via glue or another adhesive. In other embodiments, the brake 240 may be formed unitarily or integrally (or integrally molded) with the syringe 220.

As noted above, the actuation member 244 is pivotally coupled to the housing 242. The actuation member 244 is configured to move or pivot with respect to housing 242 into a plurality of positions. For example, as will be described in more detail below, the actuation member 244 may pivot or move into 3, 4, 5, or more different positions with respect to the housing 242.

In the illustrated embodiment, the housing 242 defines an opening or lumen 262 and the actuation member 244 defines an opening or lumen 264. The actuation member 244 is pivotally coupled to the housing 242 via a pin or rod 266 that extends through the opening or lumen 262 defined by the housing 242 and the opening or lumen 264 defined by the actuation member 244. Accordingly, the actuation member 244 pivots with respect to the housing 242 about an axis defined by the pin or rod 266.

In the illustrated embodiment, the actuation member 244 is biased into a first or brake position (as illustrated in FIG. 2) with respect to the housing 242. The brake 240 includes a spring member 272 that biases the actuation member 244 into its first position with respect to the housing 242. The actuation member 244 defines an opening or lumen 274. The spring member 272 is disposed within the opening or lumen 274 and contacts a surface of the housing 242. In the illustrated embodiment, a set screw 276 is disposed within the opening or lumen 274 to retain the spring member 272 in place and provide a contact surface for the spring member 272.

A user, such as a physician, may depress or push on end portion 292 of the actuation member 244 to overcome the bias of the spring member 272 and pivot or move the actuation member 244 with respect to the housing 242. Thus, the actuation member 244 may be moved from its first position to another of its positions as will be described in more detail below. In the illustrated embodiment, the actuation member 244 includes a receiving portion 294 that is configured to receive a thumb or finger of the user (physician). Specifically, the user may move or depress the receiving portion in the direction of arrow C. In the illustrated embodiment, the actuation member is biased in a direction opposite that of arrow C.

The actuation member 244 of the brake 240 includes a contact portion 291 that is configured to selectively contact the plunger 224 of the syringe 220. In the illustrated embodiment, the contact portion 291 defines a recess 293 that is configured to receive a portion of the plunger 224. The contact portion 291 also includes a pad or a brake pad 295. The pad or brake pad 295 may be formed of a softer or flexible material and may help facilitate the creation of frictional force on the plunger 224 when the actuation member 244 contacts the plunger 224.

The movement of the plunger 224 with respect to the body 222 may be controlled by the actuation member 244. In the illustrated embodiment, the actuation member 244 is configured to prevent or help prevent movement of the plunger 224 with respect to the body 222 when the contact portion 291 of the actuation member 244 is contacting the plunger 224. The actuation member 244 may slightly contact the plunger 224 and to slow the movement of the plunger 224 with respect to the body 222.

The actuation member 244 may be pivoted or moved with respect to the housing 242 into a plurality of different positions, and thus, may be moved to different positions with respect to the plunger 224. The actuation member 244 may be moved into a first position (as illustrated in FIG. 2) to prevent movement of the plunger 224 with respect to the body 122, a second position (a small movement in the direction of arrow B in FIG. 2) to slow movement of the plunger 224 with respect to the body 222, and a third position (a larger movement in the direction of arrow B in FIG. 2) to not contact the plunger 224 or otherwise interfere with the movement of the plunger 224 with respect to the body 222.

Figure 12:
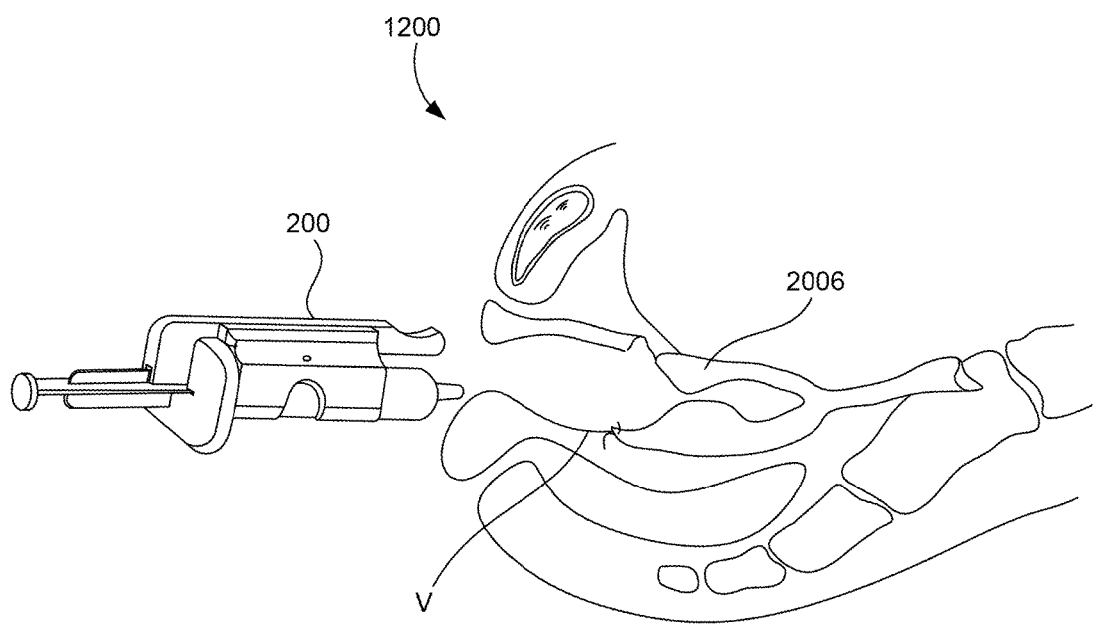
FIG. 12 is a schematic illustration of a medical device according to an embodiment of the invention being inserted into a body of a patient.

FIG. 12 schematically illustrated the device 200 being inserted into a pelvic region of a patient. The device 200 may be used to perform a dissection procedure, such as a hydrodissection procedure, within a body of a patient. The dissection procedure may be done in conjunction with a procedure to place an implant within the body of the patient. For example, the dissection procedure may be done in conjunction with placing a mesh implant, such as a sacrocolpopexy implant 2006 as shown in FIG. 12, within the body of the patient. The sacrocolpopexy implant 2006 has one end portion that is coupled to the walls of the vagina V of the patient and has another end portion that is coupled to the sacrum or tissue proximate the sacrum.

In some embodiments, the hydrodissection procedure is done by inserting the device 200 through a vaginal incision. The procedure may be used to dissect tissue in the pelvic region of the patient such as tissue proximate or close to the vagina and bladder of the patient. In some cases, the dissection procedure creates space within the body for the implant to be disposed or placed within.

Figure 13:
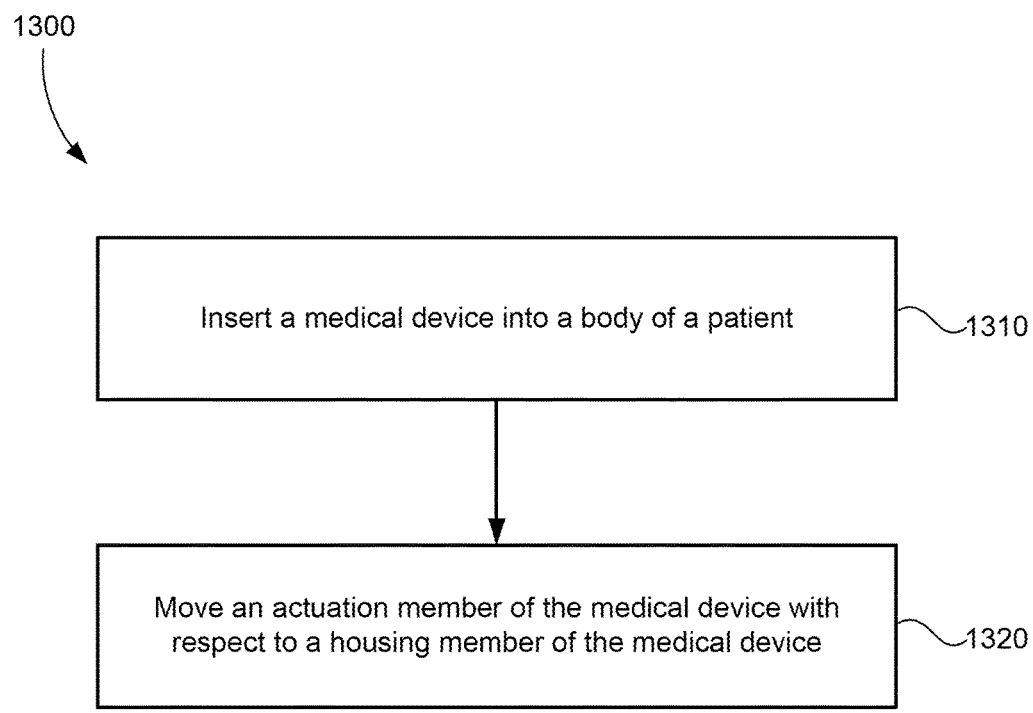
FIG. 13 is a flow chart of a method according to an embodiment of the invention.

FIG. 13 is a flow chart of a method 1300 according to an embodiment of the invention. The syringe 220 of the device 200 may be used to collect or suck up a fluid such as water or a saline solution. This may be done by inserting a distal end portion of the needle member 226 of the syringe into the fluid and retracting or moving the plunger 224 proximally with respect to the body 222. Once the fluid is loaded into the syringe 220, (at 1310) a portion of the syringe 220, such as the distal end portion of the needle member 226 of the syringe 220 may be inserted into the body of the patient. Specifically, the needle member 226 of the syringe 220 may be inserted into the body of the patient while the brake 240 is preventing or helping to prevent movement of the plunger 224 with respect to the body 222. For example, the actuation member 244 of the brake 240 may be in its first position with respect to the housing 242 while the needle member 226 is inserted into the body of the patient. In some embodiments, the brake 240 remains outside of the body of the patient when the needle is inserted into the body of the patient. In some embodiments, the needle member 226 may be inserted into the body of the patient via the vagina of the patient (such as a vaginal incision).

Once the device 200 is appropriately placed within the body of the patient (such as at the desired dissection location), (at 1320) the physician may move the actuation member 244 to disengage or move away from the plunger 224. With the actuation member 244 in this position the plunger 224 may move with respect to the body 222 and force or eject the fluid from the syringe 220. In some embodiments, the ejection of the fluid from the syringe 220 into the body of the patient dissects the tissue disposed proximate the distal end of the needle member 226 of the syringe 220. In some embodiments, the movement of the actuation member 244 with respect to the plunger 224 allows for a controlled dissection of bodily tissue. For example, the actuation member 244 may be moved completely away from the plunger 224 to allow the plunger 224 to move freely or fast with respect to the body 222 and quickly eject the fluid or the actuation member 244 may be moved to a position of slight contact with the plunger 224 to allow the plunger 224 to move more slowly with respect to the body 222 and more slowly eject the fluid from the syringe 220.

In some embodiments, a medical device includes a break having a housing member and an actuation member. The housing member having a receiving portion and being configured to be removably coupled to a syringe. The actuation member being movably coupled to the housing member.

In some embodiments, the actuation member is pivotally coupled to the housing member. In some embodiments, the actuation member is pivotally coupled to the housing member and is configured contact a plunger of the syringe. In some embodiments, the actuation member is movably coupled to the housing member and is configured to move from a first position with respect to the housing member to a second position with respect to the housing member, the actuation member being biased to its first position. In some embodiments, the actuation member is pivotally coupled to the housing member and is configured to move from a first position with respect to the housing member to a second position with respect to the housing member, the actuation member being spring biased to its first position.

In some embodiments, the housing member defines a slot extending along a longitudinal axis of the housing member, the slot being configured to receive a portion of the syringe to removably couple the housing member to the syringe. In some embodiments, the receiving portion includes a contact portion, the contact portion of the actuation member is configured to contact a plunger of the syringe. In some embodiments, the housing member is configured to be removably coupled to a body portion of the syringe and the actuation member is configured to contact a plunger of the syringe.

In some embodiments, a medical device includes a syringe having a body portion and a plunger movably coupled to the body portion; and a break having a housing member and an actuation member, the housing member coupled to the syringe, the actuation member being movably coupled to the housing member.

In some embodiments, the actuation member is pivotally coupled to the housing member. In some embodiments, the actuation member is pivotally coupled to the housing member and is configured contact the plunger of the syringe to help prevent movement of the plunger with respect to the body portion of the syringe. In some embodiments, the actuation member is movably coupled to the housing member and is configured to move from a first position with respect to the housing member to a second position with respect to the housing member, the actuation member being biased to its first position. In some embodiments, the actuation member is pivotally coupled to the housing member and is configured to move from a first position with respect to the housing member to a second position with respect to the housing member, the actuation member being spring biased to its first position.

In some embodiments, the receiving portion includes a slot extending along a longitudinal axis of the housing member, the slot being configured to receive a portion of the syringe to removably couple the housing member to the syringe.

In some embodiments, the actuation member includes a contact portion, the contact portion of the actuation member is configured to contact a plunger of the syringe.

In some embodiments, the housing member is configured to be removably coupled to the body portion of the syringe and the actuation member is configured to contact the plunger of the syringe.

In some embodiments, a method includes inserting a medical device into a body of the patient, the medical device including a syringe having a body portion and a plunger movably coupled to the body portion, and a break having a housing member and an actuation member; and moving the actuation member with respect to the housing to allow the plunger syringe to move with respect to the body portion of the syringe.

In some embodiments, the moving the actuation member includes pivoting the actuation member with respect to the housing member.

In some embodiments, the method includes creating a vaginal incision. In some embodiments, the method includes creating a vaginal incision, and the inserting the medical device includes inserting the medical device into the body of the patient via the vaginal incision.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
   a brake having a housing member and an actuation member, the housing member being configured to be removably coupled to a syringe having a plunger, the plunger including a projecting member, at least a portion of the projecting member being disposed within the syringe when delivering fluid to a patient,
   the housing member including a first arm and a second arm, the first arm and the second arm configured to receive and couple the brake to the syringe, the first arm including a curved surface, the second arm including a curved surface, the actuation member being movably coupled to the housing member, the actuation member including a contact portion, the contact portion defining a recess configured to receive a portion of projecting member of the plunger, the contact portion including a brake pad, the brake pad configured to contact the plunger and prevent movement of the plunger with respect to the housing member, and
   the actuation member configured to move from a first position to a second position, the brake pad configured to resist movement of the portion of the plunger through the recess when the actuation member is in the first position.

2. The medical device of claim 1, wherein the actuation member is pivotally coupled to the housing member via a pin, the actuation member configured to pivot with respect to the housing member about an axis defined by the pin.

3. The medical device of claim 1, wherein the actuation member is biased to the first position.

4. The medical device of claim 1, wherein the actuation member is pivotally coupled to the housing member, the actuation member being spring biased to the first position.

5. The medical device of claim 1, wherein the actuation member includes a first end portion and a second end portion, the first end portion of the actuation member including the contact portion having the brake pad, the second end portion of the actuation member including a receiving portion configured to receive a thumb or finger of a user.

6. The medical device of claim 1, wherein the housing member is configured to be removably coupled to a body portion of the syringe, the syringe including a loss of resistance syringe.

7. The medical device of claim 1, wherein the contact portion defining the recess is configured to receive a portion of the plunger in a direction that is parallel to a sliding direction of the plunger.

8. A medical device, comprising:
   a syringe having a body portion and a plunger disposed within and movably coupled to the body portion, the plunger being disposed at a proximal end portion of the syringe and a needle tip at a distal end portion of the syringe; and a brake having a housing member and an actuation member, the housing member coupled to the syringe having a plunger, the plunger including a projecting member, at least a portion of the projecting member being disposed within the syringe when delivering fluid to a patient, the housing member including a first arm and a second arm, the first arm and the second arm configured to receive and couple the brake to the syringe, the first arm including a curved surface, the second arm including a curved surface, the actuation member being movably coupled to the housing member, the actuation member including a contact portion, the contact portion defining a recess configured to receive a portion of the plunger, the contact portion including a brake pad, the brake pad configured to contact the portion of the plunger, and the actuation member configured to move from a first position to a second position, the brake pad configured to resist movement of the portion of the plunger through the recess when the actuation member is in the first position, and the brake pad configured to contact the portion of the plunger through the recess when the actuation member is in the second position, the actuation member includes a receiving portion configured to receive a finger or thumb of a user, the receiving portion being disposed at a distal end portion of the actuation member.

9. The medical device of claim 8, wherein the actuation member is pivotally coupled to the housing member via a pin.

10. The medical device of claim 8, wherein the actuation member is biased to the first position.

11. The medical device of claim 8, wherein the actuation member is pivotally coupled to the housing member, the actuation member being spring biased to the first position.

12. The medical device of claim 8, wherein the actuation member includes a first end portion and a second end portion, the first end portion of the actuation member including the contact portion having the brake pad, the second end portion of the actuation member including a receiving portion configured to receive a thumb or finger of a user.

13. The medical device of claim 8, wherein the housing member is configured to be removably coupled to the body portion of the syringe.

14. A method, comprising:

inserting a medical device into a body of the patient, the medical device including a syringe having a body portion and a plunger disposed within and movably coupled to the body portion, the plunger including a projecting member, at least a portion of the projection member being disposed within the syringe when delivering fluid to a patient, and a brake having a housing member and an actuation member, the housing member including a first arm and a second arm, the first arm and the second arm configured to receive and couple the brake to the syringe, the first arm including a curved surface, the second arm including a curved surface, the actuation member including a contact portion, the contact portion defining a recess configured to receive a portion of the projecting member of the plunger, the contact portion including a brake pad, the brake pad configured to contact the plunger and prevent movement of the plunger with respect to the housing member, the actuation member being biased to a first position with respect to the housing member, the brake pad resisting movement of the portion of the plunger through the recess when the actuation member is in the first position; and moving the actuation member to a second position with respect to the housing, the portion of the plunger being disposed outside the recess when in the second position to allow the plunger to move with respect to the body portion of the syringe.

15. The method of claim 14, wherein the moving the actuation member includes pivoting the actuation member with respect to the housing member.

16. The method of claim 14, further comprising:
creating a vaginal incision.

17. The method of claim 14, further comprising:
creating a vaginal incision,
the inserting the medical device includes inserting the medical device into the body of the patient via the vaginal incision.

18. The method of claim 14, wherein the actuation member includes a first end portion and a second end portion, the first end portion of the actuation member including the contact portion having the brake pad, the second end portion of the actuation member including a receiving portion configured to receive a thumb or finger of a user,
wherein the moving includes depressing the receiving portion by the user causing the brake pad to move away from the portion of the plunger.

* * * * *